United States Patent
Cohen et al.

(10) Patent No.: US 7,463,345 B2
(45) Date of Patent: Dec. 9, 2008

(54) METHOD FOR CORRELATING SPECTROSCOPIC MEASUREMENTS WITH DIGITAL IMAGES OF CONTRAST ENHANCED TISSUE

(75) Inventors: Jeffrey K. Cohen, Pittsburgh, PA (US); John Maier, Pittsburgh, PA (US); Robert Schweitzer, Pittsburgh, PA (US)

(73) Assignee: Chemimage Corporation, Pittsburgh, PA (US)

(*) Notice: Subject to any disclaimer, the term of this patent is extended or adjusted under 35 U.S.C. 154(b) by 91 days.

(21) Appl. No.: 11/647,195

(22) Filed: Dec. 29, 2006

(65) Prior Publication Data
US 2007/0127022 A1 Jun. 7, 2007

Related U.S. Application Data

(63) Continuation-in-part of application No. 11/527,839, filed on Sep. 27, 2006.

(60) Provisional application No. 60/720,709, filed on Sep. 27, 2005, provisional application No. 60/754,798, filed on Dec. 29, 2005.

(51) Int. Cl.
*G01J 3/26* (2006.01)

(52) U.S. Cl. .......................................... 356/73; 356/326

(58) Field of Classification Search ................. 356/326, 356/73
See application file for complete search history.

(56) References Cited

U.S. PATENT DOCUMENTS

| | | | |
|---|---|---|---|
| 6,690,464 B1 * | 2/2004 | Lewis et al. | 356/326 |
| 2006/0050278 A1 * | 3/2006 | Treado et al. | 356/417 |
| 2006/0155195 A1 * | 7/2006 | Maier et al. | 600/476 |
| 2007/0070343 A1 * | 3/2007 | Cohen et al. | 356/301 |
| 2007/0244395 A1 * | 10/2007 | Wang et al. | 600/476 |

* cited by examiner

*Primary Examiner*—Kara E Geisel
(74) *Attorney, Agent, or Firm*—Duane Morris LLP

(57) ABSTRACT

A system and method of correlating Raman measurements with digital images of a treated sample to classify the disease state of the sample. A spectroscopic data set is obtained for the sample positioned in the field of view of a spectroscopic device. Information about the field of view is stored. The sample is removed from the field of view and treated. The treated sample is repositioned in the field of view using the stored information. A digital image of the treated sample is obtained and the spectroscopic data set is linked with the digital image. A database is provided having a plurality of spectroscopic data sets. Each data set is linked to a corresponding digital image, and associated with the known sample. Each corresponding digital image is associated with the known treated samples. The database is searched to identify and match a data set of a known sample and the sample.

11 Claims, 14 Drawing Sheets

FIG. 5C 2930 cm⁻¹
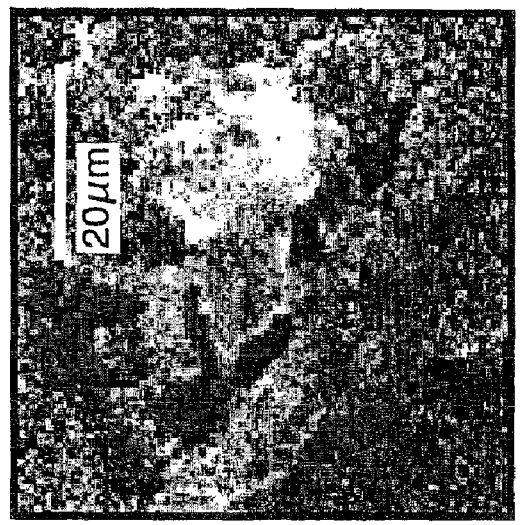
FIG. 5B 1650 cm⁻¹
FIG. 5A 1450 cm⁻¹

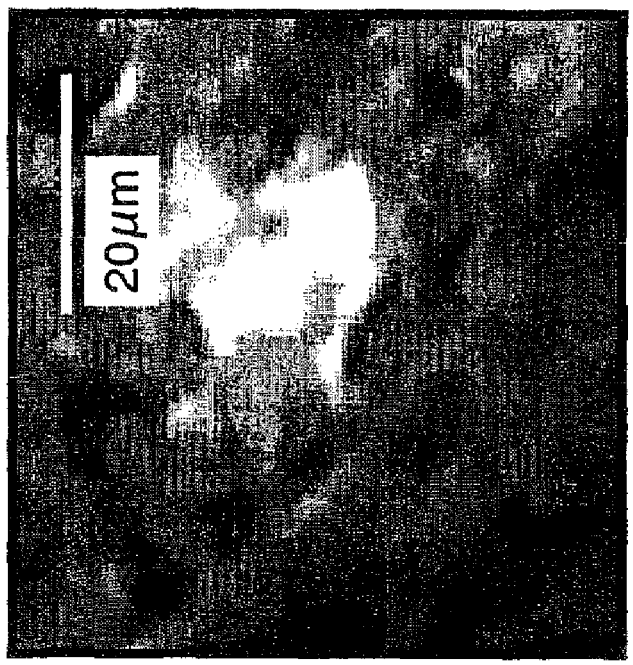
FIG. 6B  570 nm
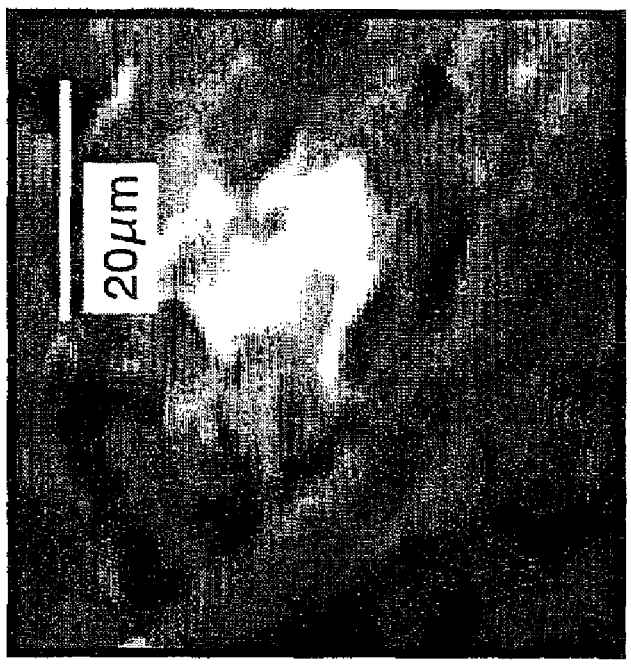
FIG. 6A  515 nm

METHOD FOR CORRELATING SPECTROSCOPIC MEASUREMENTS WITH DIGITAL IMAGES OF CONTRAST ENHANCED TISSUE

RELATED APPLICATIONS

The instant application is a continuation-in-part (CIP) of application Ser. No. 11/527,839 filed Sep. 27, 2006, entitled "Method for Correlating Spectroscopic Measurements with Digital Images of Contrast Enhanced Tissue", which claims the filing-date benefit of Provisional Application No. 60/754,798, filed Sep. 27, 2005, entitled "Method for Correlating Raman Measurements with Digital Images of Stained Tissue"; the instant application also claims the filing-date benefit of Provisional Application No. 60/754,798, filed Dec. 29, 2005, entitled "Customized Spectral Display of User-Selected Regions of Interest"; the specification of each of the above-identified applications is incorporated herein by reference in its entirety.

FIELD OF DISCLOSURE

The present invention relates generally to a method and system to use spectroscopic measurements to classify a disease state through a correlation of spectroscopic measurements and digital images.

BACKGROUND

Spectroscopy and imaging has held promise for adding quantitative and objective analysis of tissue samples. However, the application of spectroscopic measurements to tissue analysis is limited by the inability to correlate the spectroscopic data with histopathology which is evident in image data. This results from the interference of traditional contrasting agents with spectroscopic measurements. The present disclosure describes an approach to overcome this limitation.

Further, current spectroscopy and chemical imaging systems do not provide a link between a brightfield or regular optical image of a field of view (FOV) and its corresponding Raman (or any other type of) chemical image. Although a user can view both of these images simultaneously, the display is disjunctive in nature. The user cannot point to a region of interest (ROI) in the optical image and view the spectral information only for that region of interest. This selective viewing feature is not available in current chemical imaging systems.

SUMMARY

The present disclosure provides for a method of correlating spectroscopic measurements with digital images of treated tissue and using the correlation to classify a disease state of a sample. A sample is positioned in a field of view of a spectroscopic device. A spectroscopic data set is obtained for the sample positioned in the field of view. The positional information about the field of view is stored. After the sample is treated with a contrast enhancing agent, the treated sample is repositioned in the field of view of the spectroscopic device using the stored positional information about the field of view. A digital image of the treated sample positioned in the field of view is obtained. The sample's spectroscopic data set is linked with the digital image by defining a transformation to map the image spatial coordinates of the digital image to the corresponding spectral spatial coordinates of the spectroscopic data.

In one embodiment, the spectroscopic data set includes a plurality of Raman spectra and a plurality of spatially accurate wavelength resolved Raman images.

In another embodiment, a database having a plurality of spectroscopic data sets is provided. Each spectroscopic data set is linked to a corresponding digital image, and each spectroscopic data set is associated with a known sample having well characterized pathology. Each corresponding digital image is associated with the known sample treated with a contrast enhancing agent. For the spectroscopic data set of the sample, the database is searched to identify a spectroscopic data set of a known sample matching the sample's spectroscopic data set.

The present disclosure further provides for a storage medium containing machine readable program code, which, when executed by a processor, causes the processor to perform a series of steps. A first spectroscopic data set is obtained for a sample positioned in a field of view of a spectroscopic device. The positional information about the field of view is stored. After the sample is treated with a contrast enhancing agent, the repositioning of the treated sample in the field of view of the spectroscopic device is monitored using the stored positional information for the field of view. A digital image of the treated sample positioned in the field of view is obtained. The digital image and the first spectroscopic data set are stored. For the first spectroscopic data set, a database having a plurality of spectroscopic data sets is searched to identify a second spectroscopic data set matching the first spectroscopic data set.

The present disclosure further provides for a system including a spectroscopic device, an imaging device, a machine readable program code containing executable program instructions; and a processor operatively coupled to the spectroscopic device and the imaging device and configured to execute the machine readable program code so as to perform a series of steps.

In one embodiment, the system further includes a database having a plurality of spectroscopic data sets and a plurality of digital images of known samples having well characterized pathology.

In another embodiment, the disclosure relates to a method comprising: obtaining a digital image of a sample having a first plurality of pixels; obtaining a spectroscopic data set of the sample, the spectroscopic data set having a second plurality of pixels; mapping the first plurality of pixels to the second plurality of pixels to associate the brightfield image of the sample with the spectroscopic data set; selecting a first region of interest from the digital image of the sample, the first region of interest defined by a subset of the first plurality of pixels; and obtaining the spectroscopic data set for the first region of interest by identifying a subset of the second plurality of pixel corresponding to the subset of the first plurality of pixels.

In still another embodiment, the disclosure relates to a system comprising: an optical device for obtaining a digital image of a sample and a spectroscopic data set for the sample, the digital image defined by a first plurality of pixels and the spectroscopic data set defined by a second plurality of pixels; and a processor programmed with instructions to: map the first plurality of pixels to the second plurality of pixels to associate the digital image with the spectroscopic data set; identify a first region of interest from the digital image of the sample, the first region of interest defined by a subset of the first plurality of pixels; and obtain the spectroscopic data set for the first region of interest by identifying a subset of the second plurality of pixel corresponding to the subset of the first plurality of pixels.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure. In the drawings:

FIGS. 5A-5C show spatially accurate wavelength resolved Raman images of kidney tissue;

FIGS. 6A-6B show spatially accurate wavelength resolved fluorescence images of kidney tissue;

DETAILED DESCRIPTION

Figure 1:
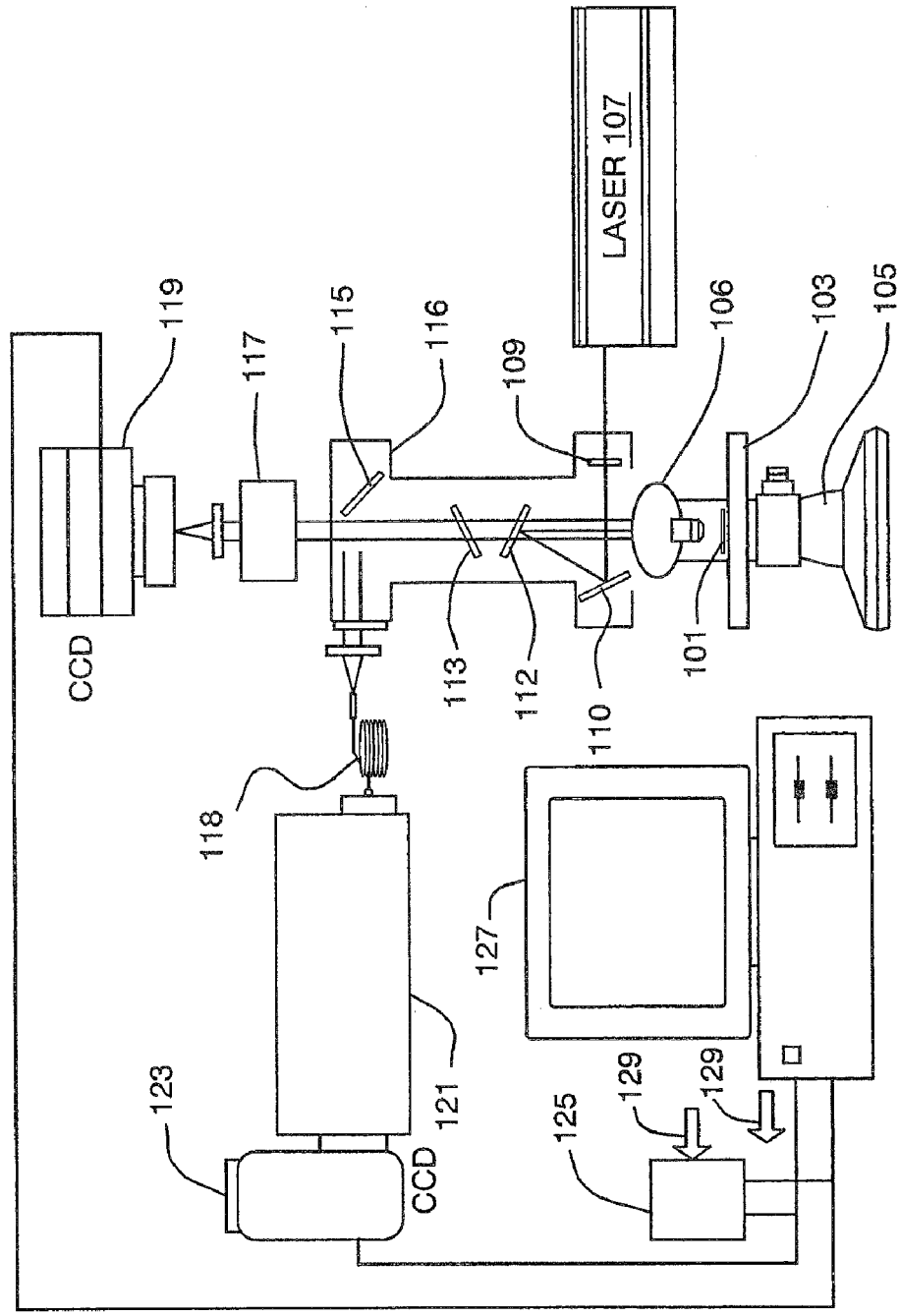
FIG. 1 schematically represents an exemplary system of the present disclosure.

Reference will now be made in detail to the preferred embodiments of the present invention, examples of which are illustrated in the accompanying drawings. Wherever possible, the same reference numbers will be used throughout the drawings to refer to the same or like parts.

The present disclosure provides for a method to correlate spectroscopic measurements of samples with the spatial locations on digital images of contrast enhanced tissue. The correlation allows a user to classify the disease state of an unknown sample. Because treating a sample with a contrast enhancing agent typically interferes with spectroscopic measurements, spectroscopic data, for the unknown sample, are obtained prior to treating the unknown with the agent. The field of view of the spectroscopic measurement is stored so that the sample may be repositioned in the same field of view for later digital image measurements. The sample is then treated with the contrast enhancing agent and the unknown sample repositioned in the previously stored field of view. An image of the contrast enhanced sample is then obtained. The image of the contrast enhanced sample is linked to the spectroscopic measurement through a procedure of defining a mathematical translation of the relative spatial coordinates of the image of the contrast enhanced sample to the corresponding spatial coordinates of the spectroscopic measurements. The spatial coordinates of the digital image and the spatial coordinates of the spectroscopic measurements may be stored in a database. Because the two independent measurements are made on the same field of view, relative positions within the two datasets will correspond to the same location on the sample. By way of example, a single point halfway between the top and bottom and halfway between the left and right of the boundaries of the digital image of the contrast enhanced sample (at the center of the digital image) corresponds to the spectral measurement halfway between the top and bottom and halfway between the left and right of the boundaries of the set of spectroscopic measurements. By way of second example, the upper right quadrant of the digital image of the contrast enhanced sample corresponds to the upper right quadrant of a wavelength resolved spectra image obtained in set of spectroscopic measurements. This mathematical translation is in relative coordinates thus, there is no requirement that both images have the same pixel size or shape.

Through this procedure, the spectroscopic measurements are effectively linked to the digital images of the contrast enhanced sample. The method allows a user to classify the disease state of an unknown sample, based on its spectroscopic data, by searching a database containing spectroscopic information for known samples with well characterized pathology. This search can be performed on selected regions of the spectral data set. The method enables the search to be focused on selected regions of the spectral data set, containing spatially accurate wavelength resolved images, where the selected regions are targeted through use of the digital image of the contrast enhanced sample which is linked to the spectral data as described above. By way of example, in a case where a field of view contains both epithelial tissue and stromal tissue, a more accurate search of the database of spectral information can be obtained by selecting a subset spectral data corresponding to the epithelial tissue to be searched against the database. This subset of the spectral data can be determined after the digital image of the contrast enhanced sample is linked to the spectral measurements. The subset of spectral data is determined by identifying the spatial coordinates for a region of interest on the digital image of the contrast enhanced sample (corresponding to the epithelium for example), making the mathematical translation to identify the corresponding region of interest in the spectral dataset. The database is searched for the spectral data corresponding to the subset of the spectral data defined by the mapping of the region of interest from the digital image of the contrast enhanced sample to the spectral data set. This subset is searched against the database for matches for the spectral character of the sample.

A digital image of the sample prior to treatment with a contrast enhancing agent may also be obtained and stored. The digital image may be used if subtle positional differences are present between the images of the treated and untreated samples. In this embodiment, the digital image of the untreated sample provides the positioning of the regions of interest to resolve any discrepancy.

As described above, the image linking scheme is a tool for selecting which subset of the spectral image data for the selected region of interest is used for disease classification through searching the database. This is described above for a manual approach to select a region of interest on the digital image which is linked to the spectral image. Automated approaches based on image segmenting could equally be applied to select a region of interest using a digital image associated with a spectral image. For instance an automated algorithm for determining which regions of a digital image correspond to the nuclei of cells could be used to select the subset of the spectral image which is compared to the database. Moreover, there is no restriction that a subset of the spectral dataset is contiguous spatially.

FIG. 1 schematically represents an exemplary system 100 used to perform the methods of the present disclosure. System 100 includes, in a single platform, an imaging device in the form of a microscope objective 106, a spectroscopic device in the form of an imaging spectrometer 117 or a dispersive spectrometer 121, a processor 127, a database 125 and a microscope stage 103. System 100 further includes laser light source 107, white light source 105, bandpass filter 109 to remove $SiO_2$ bands arising from a laser excitation fiber optic. The laser light is directed to a band reject optical filter 110 and propagated through an imaging objective 106 to illuminate the sample 101. Objective 106 collects photons emanating from the sample 101. Notch filters 112 and 113 reject light at the laser wavelength.

Though the discussion herein focuses on the system illustrated in FIG. 1, the practice of the method of this disclosure is not limited to such a system. An alternative system with the ability to deliver digital images and spectroscopic data sets is described in U.S. Pat. No. 7,046,359 entitled "System and Method for Dynamic Chemical Imaging" which is incorporated herein by reference in its entirety.

Sample 101 is an unknown sample for which a user would like to classify its disease state. Sample 101 may include a variety of samples such as tissue, tissue microarray, protein microarray, DNA microarray, and western blot. In one embodiment, sample 101 includes tissue. In another embodiment, the tissue includes kidney tissue, prostate tissue, lung tissue, colon tissue, bone marrow tissue, brain tissue, red blood tissue, breast tissue and cardiac muscle tissue.

Figure 2A:
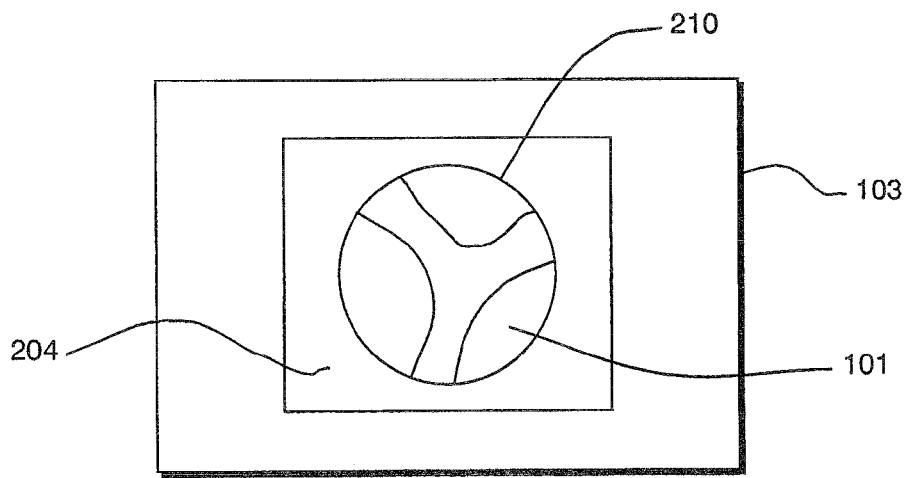
FIGS. 2A-2C illustrate the operation of an exemplary device used in the system of the present disclosure.
Figure 2B:
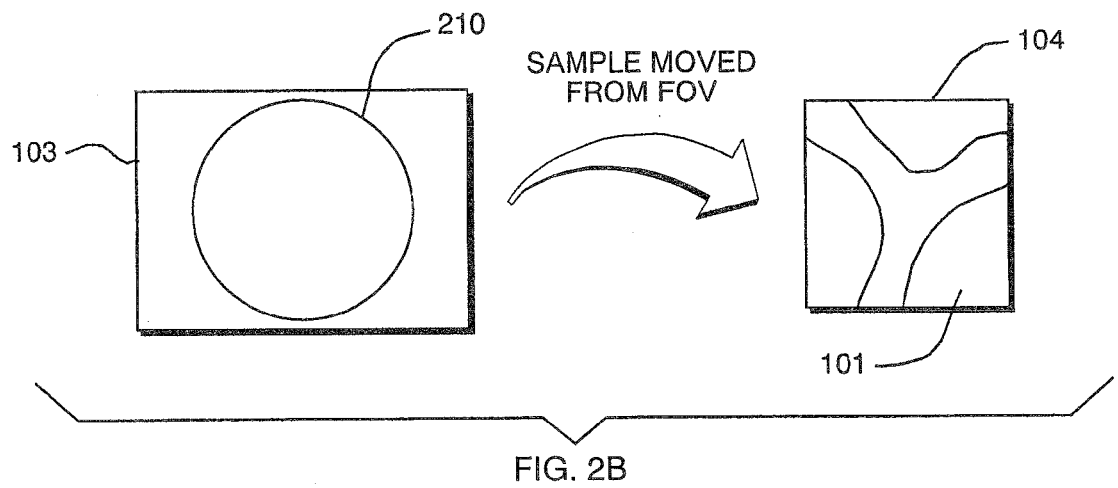
Figure 2C:
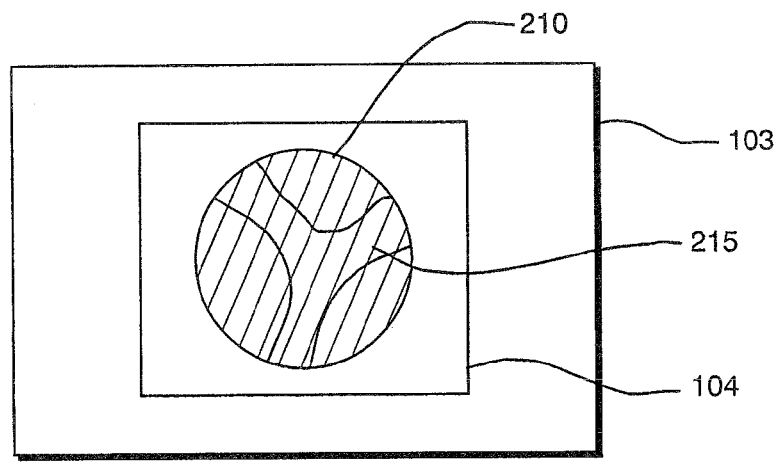

FIGS. 2A-2C illustrate sample 101 supported on a substrate 204 which is positioned on an exemplary XYZ translational microscope stage 103. Microscope stage 103 includes a movable stage such as an automated XYZ translational microscope stage 103 which functions to position the sample 101 in field of view 210 of the collection optics of spectroscopic devices 117 or 121. Sample 101 is positioned in the field of view 210 of spectroscopic device 117, FIG. 2A. Imaging device 106 and spectroscopic devices 117 and 121 are aligned to have the same field of view 210. The positional information for the field of view 210 is stored for later reference. In one embodiment, the positional information is the center of the field of view relative to some origin fixed on the sample holder. Spectroscopic devices 117 and 121 are used to obtain a spectroscopic data set for sample 101 positioned in the field of view 210. In one embodiment, spectroscopic devices 117 or 121 are used to obtain Raman data sets for a tissue sample and imaging device 106 is used to obtain digital images of the tissue sample. In another embodiment, spectroscopic devices 117 or 121 are used to obtain fluorescence datasets for a sample and imaging device 106 is used to obtain digital images of the tissue sample. Sample 101 is then moved from the field of view 210 using the XYZ translational microscope stage, as shown in FIG. 2B. While sample 101 is positioned outside the field of view 210, sample 101 is treated with a contrast enhancing agent. The contrast enhancing agent includes a stain, a haematoxylin and eosin stain, phosphotungstic acid haematoxylin, silver nitrate, silver metal, gold ions, gold metal, osmium (VIII) oxide and immunohistochemically targeted fluorescent stains. In one embodiment, the contrast enhancing agent includes a haematoxylin or eosin stain. The treated sample 215 is repositioned within the field of view 210 of spectroscopic devices 117 and 121 using the stored positional information, FIG. 2C. The imaging device 106 is used to obtain a digital image of the treated sample 215. In one embodiment, imaging device 106 is used to obtain a digital image of a tissue sample treated with a haematoxylin stain. By these steps, a user is able to obtain spectroscopic data of a sample before treatment with the contrast enhancing agent and digital images of the sample after treatment with the contrast enhancing agent. The spectroscopic data is obtained from the same spatial locations as observed in the digital images by storing the positional information of the field of view of spectroscopic devices 117 and 121.

To obtain a digital image, sample 101 is illuminated using a broad band light source 105, as illustrated in FIG. 1. In one embodiment, the white light source 105 is located under the sample 100 where system 100 operates a transmittance image mode. In a second embodiment, the white light source 105 is located above the sample 101 when system 100 operates in reflectance image mode. The transmitted or reflected light from the sample 101, positioned on the XYZ translational microscope stage 103, is collected using microscope objective 106. In one embodiment, microscope objective 106 includes an infinity-corrected microscope objective. The resulting digital image is detected by a CCD detector (not shown) and stored in database 125.

Sample 101 is also illuminated with a laser light source 107. Light source 107 can include any conventional photon source, including laser, LED, and other IR or near IR devices. Light source 107 may also be selected to provide evanescence illumination of the sample. In one embodiment, the line width of the laser light source 107 is in the range of about 15-25 $cm^{-1}$. In another embodiment, laser epi-illumination is provided by light source 107, such as a Spectra Physics Millenia II Nd:$YVO_4$ laser beamed directly into the microscope optic. The monochromatic light reaching sample 101 illuminates the sample and photons are either scattered or emitted from different locations on or within the sample. The term emitted includes a wide range of optical processes including fluorescence, phosphorescence, photoluminescence, electroluminescence, chemiluminescence, sonoluminescence, thermoluminescence and even upconversion. Emitted photons or Raman scattered photons are collected by microscope objective 106 and directed to spectrometer 121 or imaging spectrometer 117.

Spectrometer 121 and imaging spectrometer 117 function to produce spectroscopic data sets of sample 101. A spectroscopic data set includes one or more of the following: a plurality of spectra and a plurality of spatially accurate wavelength resolved spectroscopic images. In one embodiment, the plurality of spectra includes a plurality of Raman spectra and the plurality of spatially accurate wavelength resolved spectroscopic images include a plurality of spatially accurate wavelength resolved Raman images. In another embodiment, the plurality of spectra includes a plurality of fluorescence spectra and the plurality of spatially accurate wavelength resolved spectroscopic images include a plurality of spatially accurate wavelength resolved fluorescence images. In yet another embodiment, the plurality of spectra includes a plurality of transmittance spectra and the plurality of spatially accurate wavelength resolved spectroscopic images include a plurality of spatially accurate wavelength resolved transmittance images. The spectroscopic data set may contain spectroscopic subsets where the subset includes a plurality of spectra for the region of interest selected from the digital image.

The plurality of spectra are obtained using dispersive spectrometer 121. A swing away mirror 115 is placed before filter 117 to redirect the emitted or Raman scattered photons to a fiber-optic 118. The other end of fiber-optic 118 is configured in a linear geometry and is focused on the entrance slit of a dispersive spectrometer 121. The plurality of spectra are detected by CCD detector 123 located at the exit focal plane of the spectrometer 121.

Referring still to FIG. 1, an imaging spectrometer 117 is used to generate the plurality of spatially accurate wavelength resolved spectroscopic images. The imaging spectrometer includes a two-dimensional tunable filter, such as electro-optical tunable filters, liquid crystal tunable filter ("LCTF") or acousto-optical tunable filter ("AOTF"). The electro-optical filter (interchangeably, tunable filters) sequentially passes the emitted or Raman scattered photons in each of a plurality of predetermined wavelength bands. The plurality of predetermined wavelength bands include specific wavelengths or ranges of wavelengths. In one embodiment, the predetermined wavelength bands include wavelengths characteristic of the sample undergoing analysis. The wavelengths that can be passed through tunable filter 140 may range from 200 nm (ultraviolet) to 2000 nm (i.e., the far infrared). The choice of tunable filter depends on the desired optical region and/or the nature of the sample being analyzed. The two-dimensional tunable filter includes a Fabry Perot angle tuned filter, an acousto-optic tunable filter, a liquid crystal tunable filter, a Lyot filter, an Evans split element liquid crystal tunable filter, a Solc liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, a liquid crystal Fabry Perot tunable filter. The tunable filer is selected to operate in one or more of the following spectral ranges: the ultraviolet (UV), visible, near infrared, and mid-infrared.

The plurality of spectra are detected by detector 123 and the plurality of spatially accurate wavelength resolved spectroscopic images are detected by detector 119. Detector 119 detects, in a spatially accurate manner, the emitted, Raman scattered or transmitted photons passed by imaging spectrometer 117. Detectors 119 and 123 may include a digital device such as for example an image focal plane array ("FPA") or CCD or CMOS sensor. The optical region employed to characterize the sample of interest governs the choice of two-dimensional array detector. For example, a two-dimensional array of silicon charge-coupled device ("CCD") detection elements can be employed with visible wavelength emitted or Raman scatter photons, while gallium arsenide (GaAs) and gallium indium arsenide (GaInAs) FPA detectors can be employed for image analyses at near infrared wavelengths. The choice of such devices depends on the type of sample being analyzed.

The spectroscopic data set and the digital image of the sample 101 are stored in database 125, shown in FIG. 1. For sample 101, its spectroscopic data set is linked with the digital image of the sample 101. In one embodiment, Raman spectroscopic data for a sample is linked to a digital image of the sample treated with haematoxylin stain and or eosin. As was discussed above, the digital image and the spectroscopic data set are linked through a transformation. The digital image, of the treated sample, may be characterized by a plurality of spatial coordinates. These spatial coordinates describe the x and y positions of the various features observed in the digital image. The spatially accurate wavelength resolved images, that are part of the spectroscopic data sets, are also characterized by a plurality of spatial spectral coordinates. The digital image and the spectroscopic data set are then linked through a transformation that maps the plurality spatial coordinates of the digital image to the corresponding plurality of spatial coordinates of the spectroscopic data set for sample 101.

Database 125 also stores a plurality of spectroscopic data sets and digital images for known samples. The known samples have well characterized pathology of various disease conditions made through pathological examination of the digital images. The disease conditions include cancer, infection, stroke, ischemia, metabolic disorder, autoimmune disorders and heart attack. In database 125, each spectroscopic data set is associated with the known sample and linked to the corresponding digital image of the known sample where the sample has been treated with a contrast enhancing agent.

To determine the spectroscopic data set or subset of sample 101 for analysis, the spatial coordinates of a region of interest are identified from the digital image of the treated sample. A corresponding region of interest is then identified for the spectroscopic data set or subset based on the transformation discussed above. The spectroscopic data set or subset includes one or more spatially accurate wavelength resolved spectroscopic images.

Processor 127 is configured to execute a machine readable program code 129 to search the database 125. For the spectroscopic data set or subset of the sample 101 under analysis, the database is searched to identify a spectroscopic data set, for a known sample having well characterized pathology, matching the spectroscopic data set of the sample 101. In one embodiment, database 125, is searched for a Raman data set for a known sample that matches the Raman spectrum of a tissue sample from a subject which is suspected of having a disease. The database can be searched using a variety of similarity metrics. The metrics include Euclidean Distance, the Spectral Angle Mapper (SAM), the Spectral Information Divergence (SID), Mahalanobis distance metric and spectral unmixing. A spectral unmixing metric is disclosed in U.S. Pat. No. 7,072,770 B1 entitled "Method for Identifying Components of a Mixture via Spectral Analysis," which is incorporated herein by reference in its entirety.

The use of Raman spectroscopy to detect diseases is disclosed in the following: U.S. patent application Ser. No. 11/269,596 entitled "Cytological Methods for Detecting Disease Conditions Such as Malignancy by Raman Spectroscopic Imaging," filed Nov. 9, 2005; U.S. patent application Ser. No. 11/000,545, filed Nov. 20, 2004, entitled "Raman Molecular Imaging for Detection of Bladder Cancer, which are incorporated by reference herein it their entirety. In one embodiment, the database is searched to determine if the tissue sample is indicative of bladder cancer by the sample's Raman spectra data sets. Cancerous bladder cells exhibit significant Raman scattering at an RS value of about 1584 $cm^{-1}$, relative to non-cancerous bladder cells. The intensity of Raman scattering at this RS values increases with increasing grade of bladder cancer. Other RS values at which Raman scattering is associated with the cancerous state of bladder cells include about 1000, 1100, 1250, 1370, and 2900 $cm^{-1}$. Furthermore, there is a generalized increase in Raman scattering at RS values in the range from about 1000 to 1650 $cm^{-1}$ and in the range from about 2750 to 3200 $cm^{-1}$ in bladder cancer cells, relative to non-cancerous bladder cells, and this generalized increase is more pronounced in the range of RS values from about 1530 to 1650 $cm^{-1}$. These RS values and ranges are useful for assessing the cancerous state of bladder cells.

Figure 3:
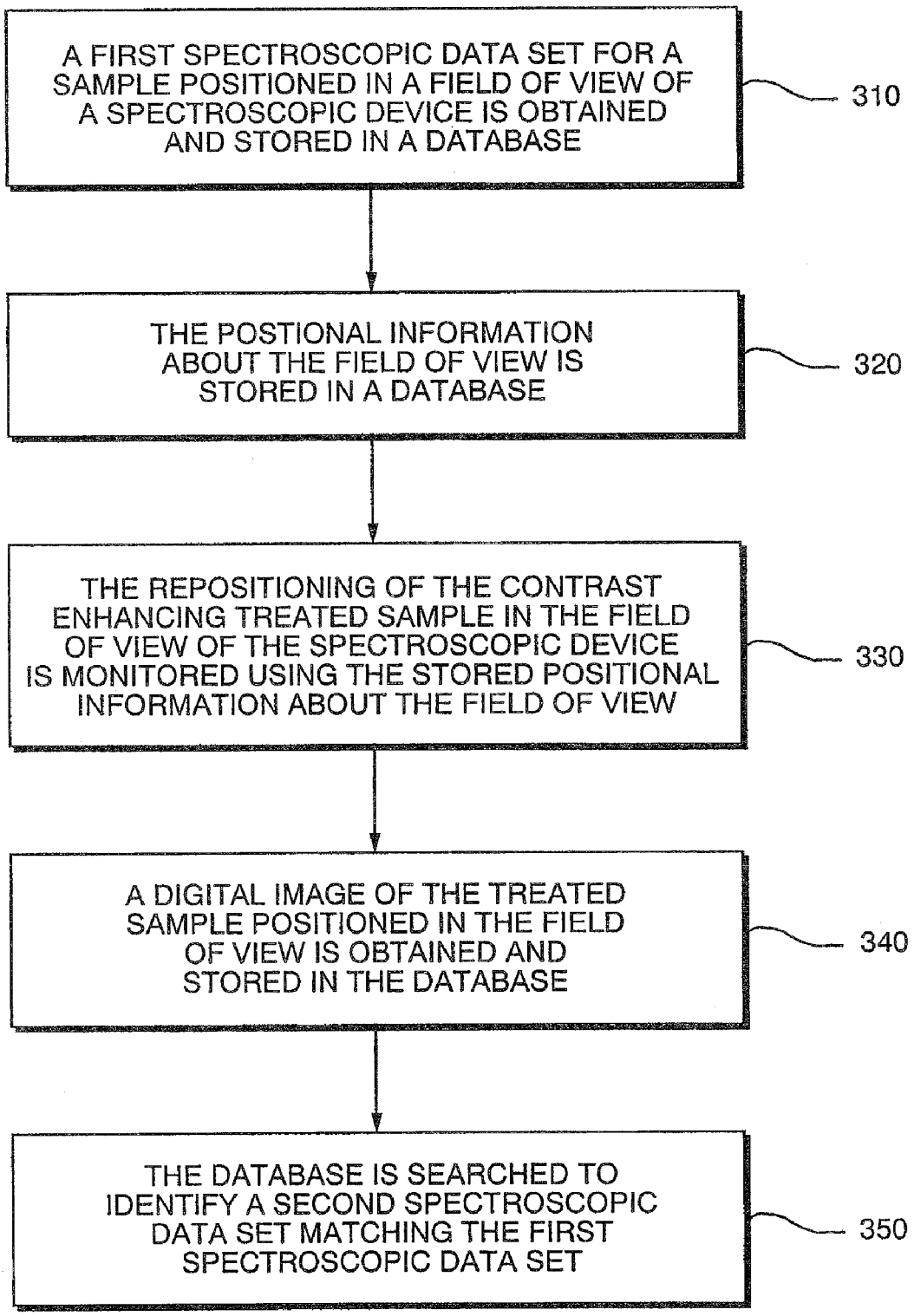
FIG. 3 is a flow chart illustrating an exemplary method of the present disclosure.

Processor 127 is also configured to execute machine readable program code containing executable program instructions to perform a variety of functions. These functions are illustrated in FIG. 3 which shows a flow chart for a method of the present disclosure. In step 310, a first spectroscopic data set for a sample positioned in a field of view of a spectroscopic device is obtained and stored in a database. In step 320, the positional information about the field of view is stored in a database. In step 330, the repositioning of the contrast enhancing treated sample in the field of view of the spectroscopic device is monitored using the stored positional information about the field of view. In step 340, a digital image of the treated sample positioned in the field of view is obtained and stored in the database. The field of view is the same field of view at that in step 310. In step 350, the database is searched to identify a second spectroscopic data set matching the first spectroscopic data set or a subset of the spectroscopic dataset chosen using the linked digital image as a guide. The second spectroscopic data set is for a known sample having well characterized pathology.

As stated, in another embodiment, the disclosure relates to a display system wherein a user can select an ROI on a digital image (intercheangeably, optical, RGB or brightfield image) and the system can display only the selected region-specific spectral information. This feature provides meaningful spectral information for the user-selected ROI only. This approach can customize user's experience when viewing and analyzing the content of the brightfield image. For example, a doctor may first view a brightfield image of a cancerous cell/tissue. However, at this point, the doctor is not concerned about the spectral image or spectral content of the entire FOV of the cell/tissue at hand. If in the digital image the doctor notices some regions of interest, then this software feature can enable the doctor to select those regions of interest and selectively view their corresponding spectral information without necessarily viewing the chemical image of the sample's entire FOV. The system allows the user a choice of when and what to view spectrally with respect to the available brightfield image.

In one embodiment, the disclosure relates to linking of a digital image of a sample with its chemical image (or its spectral data set) taken by using any molecular spectroscopy technique such as Raman, fluorescence, near-IR, or mid-IR spectroscopy) in a spatially corresponding manner. The terms digital image, optical image and RGB brightfield image are used herein interchangeably.

The spatial correspondence between a sample's brightfield image and its Raman spectral image (chemical image) must be preserved. In other words, the digital image and the Raman image must be of the same field of view (FOV). The spatial-mapping or pixel-by-pixel linking/scaling may be performed in software using the electronic pixel data available for the RGB and chemical images for the same FOV. The relevant electronic data may be generated using a conventional chemical imaging system. Using a chemical imaging system, in one embodiment, a user can first take the brightfield image of the desired FOV of the sample at hand. Then, the user can change the optics in the system to take the Raman chemical image of the same FOV. In another embodiment, this manual task of switching optics may be eliminated through and automated switching option on the device taking the images.

The size of the brightfield image may be of 512×512 pixels. The chemical image may be of the same pixel size or may be of a different pixel size. When the pixel sizes of both images are identical, then there will be a 1-to-1 mapping between the two images. However, when pixel sizes are different, then the software according to one embodiment of the disclosure, may scale the mapping accordingly. For example, if the brightfield image is of 512×512 size while the Raman image is of 128×128 size, then the software can map a location in the brightfield image to its spatially corresponding location in the Raman image in a scaled manner. By way of another example, if an ROI (Region of Interest) in the brightfield image is between pixels 256-260 in the X-direction (counting from the left-hand side of the image) and between pixels 400-420 in the Y-direction (counting from the top of the image), then the software may construe that to mean that the ROI is between the scaled locations of 0.5 (256/512=0.5) to 0.508 (260/512=0.508) in the X-direction and between the scaled locations of 0.781 (400/512=0.781) and 0.82 (420/512=0.82) in the Y-direction. This scaled representation can correspond to the following Raman image locations in the spatially corresponding Raman chemical image: between pixels 64 (128×0.5=64) and 65 (128×0.508=65) in the X-direction of the 128×128 size Raman image, and between pixels 100 (128×0.781=100) and 105 (128×0.82=105) in the Y-direction of the 128×128 Raman image. Similarly, other regions of interest may be scaled to the spatially corresponding chemical image.

Figure 11:
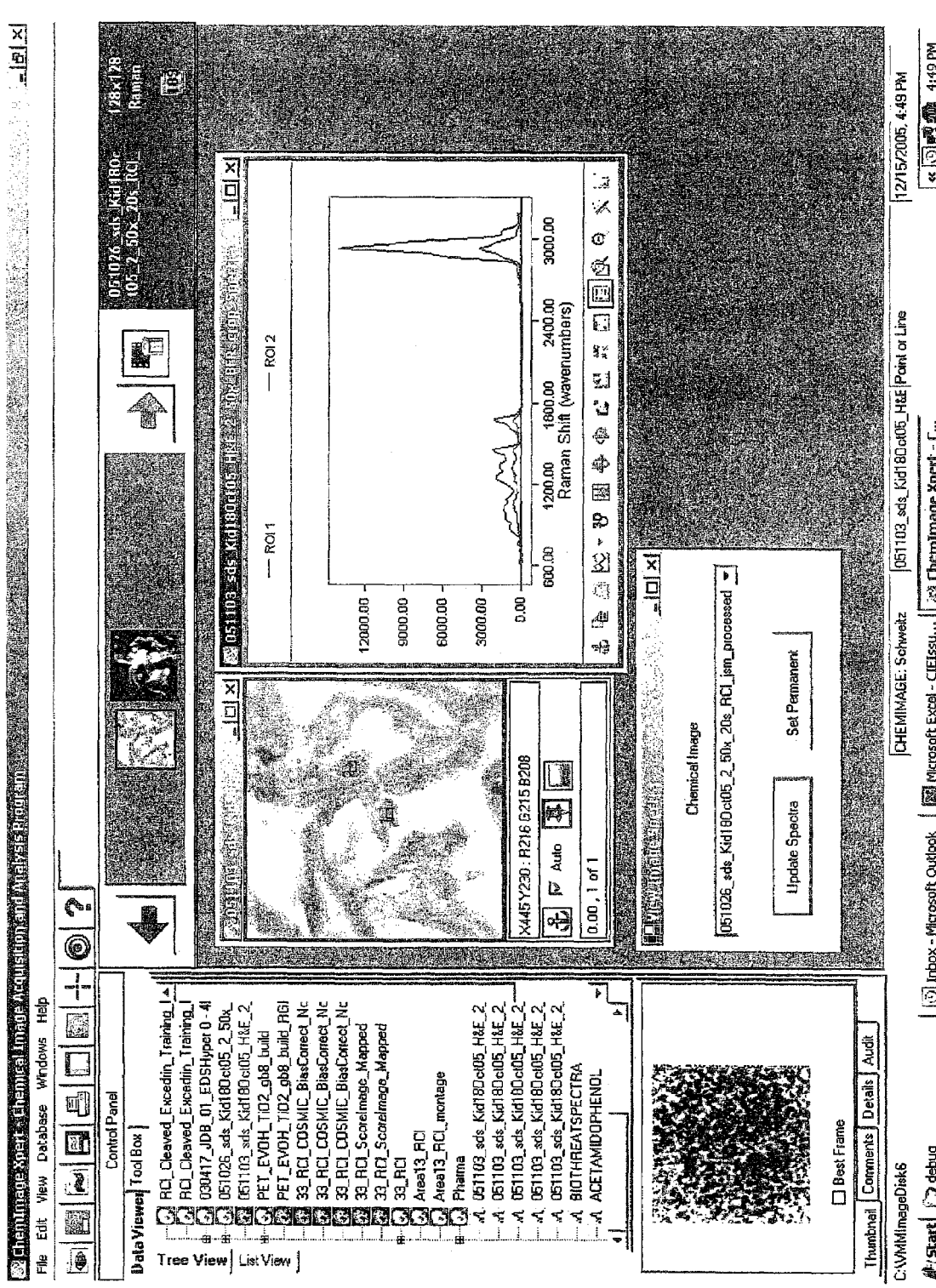
FIG. 11 shows an exemplary implementation according to one embodiment of the disclosure.

FIG. 11 depicts a screenshot showing various windows that may be generated according to one embodiment of the disclosure. In the right hand portion of the main window of the screenshot in FIG. 11, a colored brightfield image of a FOV of a sample (a kidney tissue sample) is shown in a separate window with two regions of interest marked by the user. Each of the first and the second regions are indicated by a box. The corresponding spectra for these regions of interest are shown in another window on the right hand side of the brightfield image. As noted before, the data for the brightfield and spectral information are obtained earlier using a chemical imaging system. These data are then processed using a chemical image acquisition and analysis program or software module, which will make relevant images displayed on the user's computer screen.

The selective spectrum viewing feature may be added to other software functionality as shown by the availability of the "View Image Spectra" function in the "User Functions" option under the "Tool Box" tab of the "Control Panel" window pane for the main software screen on the left-hand side in FIG. 11.

In one embodiment, the View Image Spectra function may be implemented in the "User Functions" DLL (Dynamic Link Library). An executable directory can be associated with the DLL. The executable file may spatially link the brightfield and chemical image data, and may also generate and display the appropriate spectrum plot for only the user-selected region(s) of interest.

With reference to FIG. 11, when the user selects the "View Image Spectra" function from the "Tool Box" tab, a separate chemical image selection window may be displayed on the screen as shown, for example, below the brightfield image in FIG. 11. This window can allow the user to manually select the chemical image that is associated with the brightfield image displayed on the screen. In an alternative embodiment, this chemical image selection functionality may be automated to allow the software to automatically choose the chemical image that spatially corresponds to and linked with the displayed brightfield image.

After selecting an appropriate chemical image, the user may continue by drawing (e.g., using a mouse and a cursor) desired regions of interest on the brightfield image. The software will then display the region-specific spectra when the "Update Spectra" function of the "View Image Spectra" selection window (shown below the brightfield image in FIG. 11) is activated. The software can display each region-specific spectrum after the region is selected. Thus, initially, when only one region is selected, then only one spectrum will be displayed. However, when a second region is selected, then that region-specific spectrum will be displayed in the same display window along with the spectrum for region-1. This process continues for each region selected on the brightfield image. It is observed here that the shape of the region selected on the brightfield image may be rectangular or square in the embodiment of FIG. 11.

In alternative embodiments, other geometrical shapes may be allowed for region selection depending on the complexity of the software module performing the mapping/scaling between the brightfield image and the corresponding chemical image.

Thus, the "View Image Spectra" function may be utilized in the following sequence of steps: (1) The user may display the desired brightfield image on the screen using the image acquisition software; (2) The user may select the "View Image Spectra" function from the "User Functions" menu; (3) The user may select the appropriate chemical image in the drop-down box in the dialog box present in the "View Image Spectra" window resulting from the selection of the "View Image Spectra" function; (4) After selecting the appropriate chemical image, the user may draw the desired one or more ROIs on the brightfield image; (5) Thereafter, the user may click on the "Update Spectra" button on the dialog box in the "View Image Spectra" window whenever the user wants to update the set of displayed spectra (e.g., when a new region is selected or when an earlier selected region is modified); (6) The user may repeat steps (4) and (5) as often as desired; (7) When a user wishes to save the region-specific spectra calculated and displayed on the user's screen or when the user wishes to use the displayed spectra in another calculation, the user may click on the "Set Permanent" button (next to the "Update Spectra" button) in the dialog box in the "View Image Spectra" window. This will allow the user to save or use the resulting spectral window in a way the user deems fit.

Figure 12:
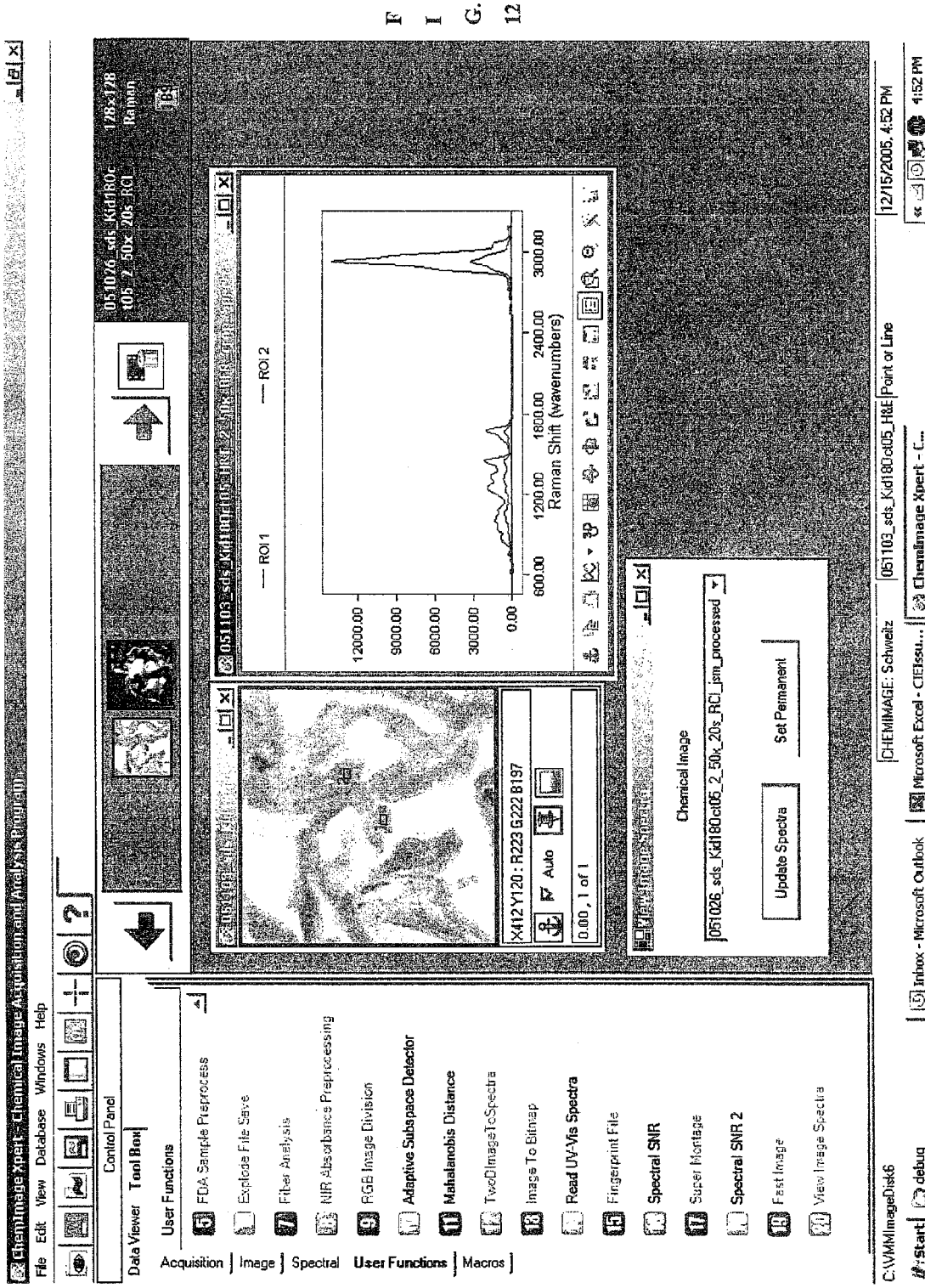
FIG. 12 shows an exemplary implementation of functional features according to one embodiment of the disclosure.

FIG. 12 furthers FIG. 11 by illustrating the content of the "Data Viewer" tab (instead of the "Tool Box" tab selected in the screenshot of FIG. 11) on the "Control Panel" window pane on the left side of the main software screen. It can be seen from the screenshot in FIG. 12 that the "Data Viewer" tab allows a user to view, in a tree format, all brightfield and chemical images being handled by the software. The user can slide up/down through the displayed selection to select the desired brightfield image as an initial step before choosing the region-specific spectrum display functionality.

In the embodiment of FIG. 12, the selected optical image can be shown highlighted in a different color in the "Tree View" of the "Data Viewer" tab. This same optical image can be shown displayed in a separate window on the right-hand window pane as in FIG. 11.

At the bottom left-hand corner of the screenshot shown in FIG. 12, a window pane can be shown with thumbnail image of a frame (discussed further below with reference to FIG. 13) of a chemical image. The thumbnail image may or may not be of the chemical image selected by the user through the "View Image Spectra" window's dialog box (shown on the right-hand portion of FIG. 12). Various other editing features can be provided along with the thumbnail image viewing option.

With respect to FIGS. 11 and 12, it is observed that a chemical image may be composed of a number of "frames" with each frame corresponding to a wavelength of interest. In one embodiment, the final Raman chemical image corresponding to the selected FOV of the sample may comprise of 189 underlying image frames of spectral information as can be seen from the number "189" shown at the top right-hand corner above the region-specific spectra window in FIGS. 11 and 12. The Raman chemical image resolution may be of 128×128 pixels as also shown above the number "189" in FIGS. 11 and 12

Figure 13:
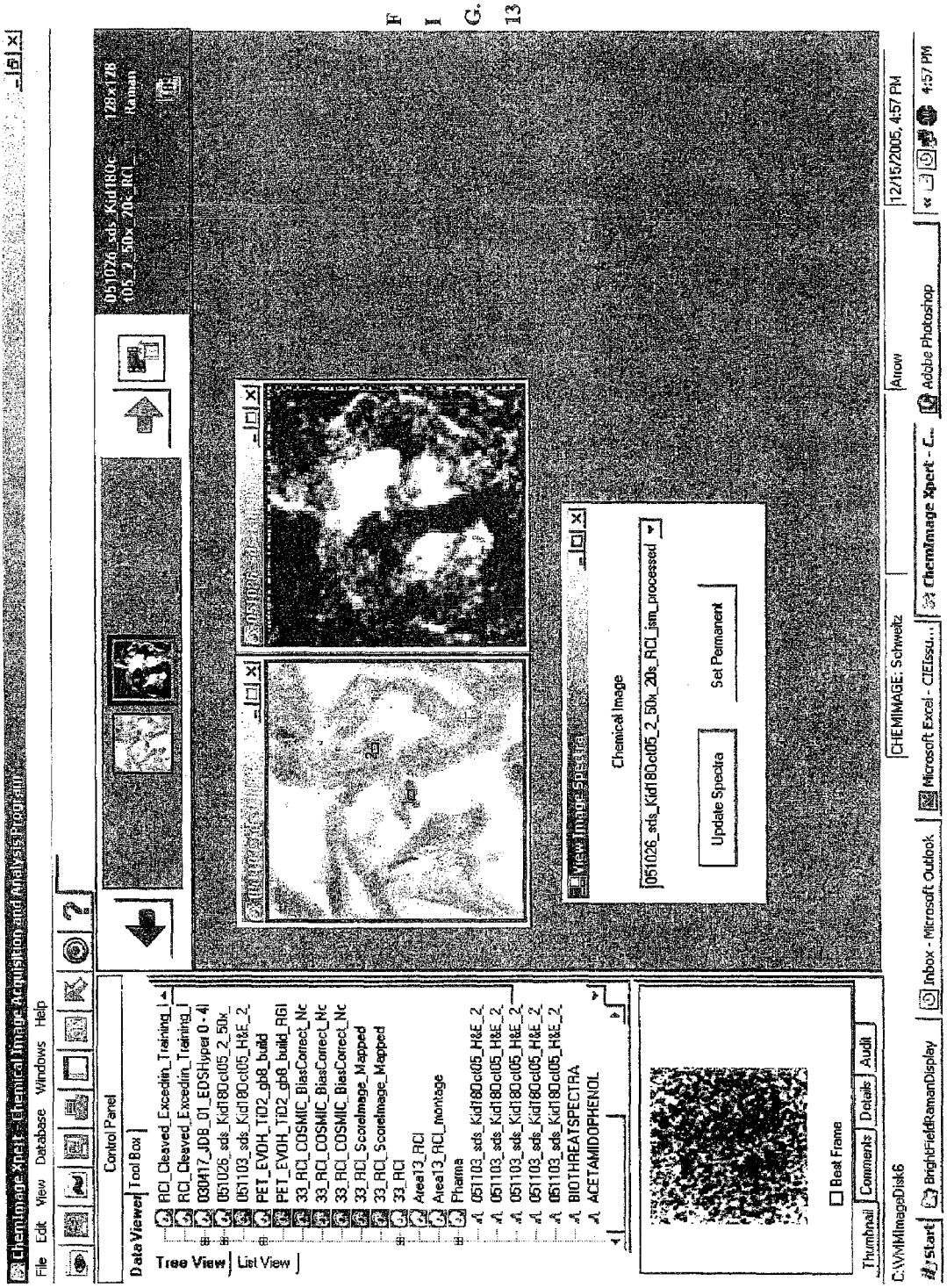
FIG. 13 shows another exemplary implementation of a frame of a Raman chemical image.

FIG. 13 illustrates a frame of the Raman chemical image displayed in a separate window on the right-hand side of and adjacent to the corresponding brightfield image of the sample's FOV. The frame displayed more fully in the separate window is that of the Raman chemical image selected by the user through the drop-down menu in the "View Image Spectra" selection window shown at the bottom of the brightfield image. In one embodiment, once the user selects a chemical image from the drop-down box, a frame (not necessarily the first of 189 frames) of that selected chemical image may automatically be displayed on the right-hand side of the screen as shown in FIG. 13. Thereafter, when the user selects the region(s) of interest on the brightfield image, a separate window showing the region-specific spectra may also be displayed along with the composite chemical image.

Figure 14:
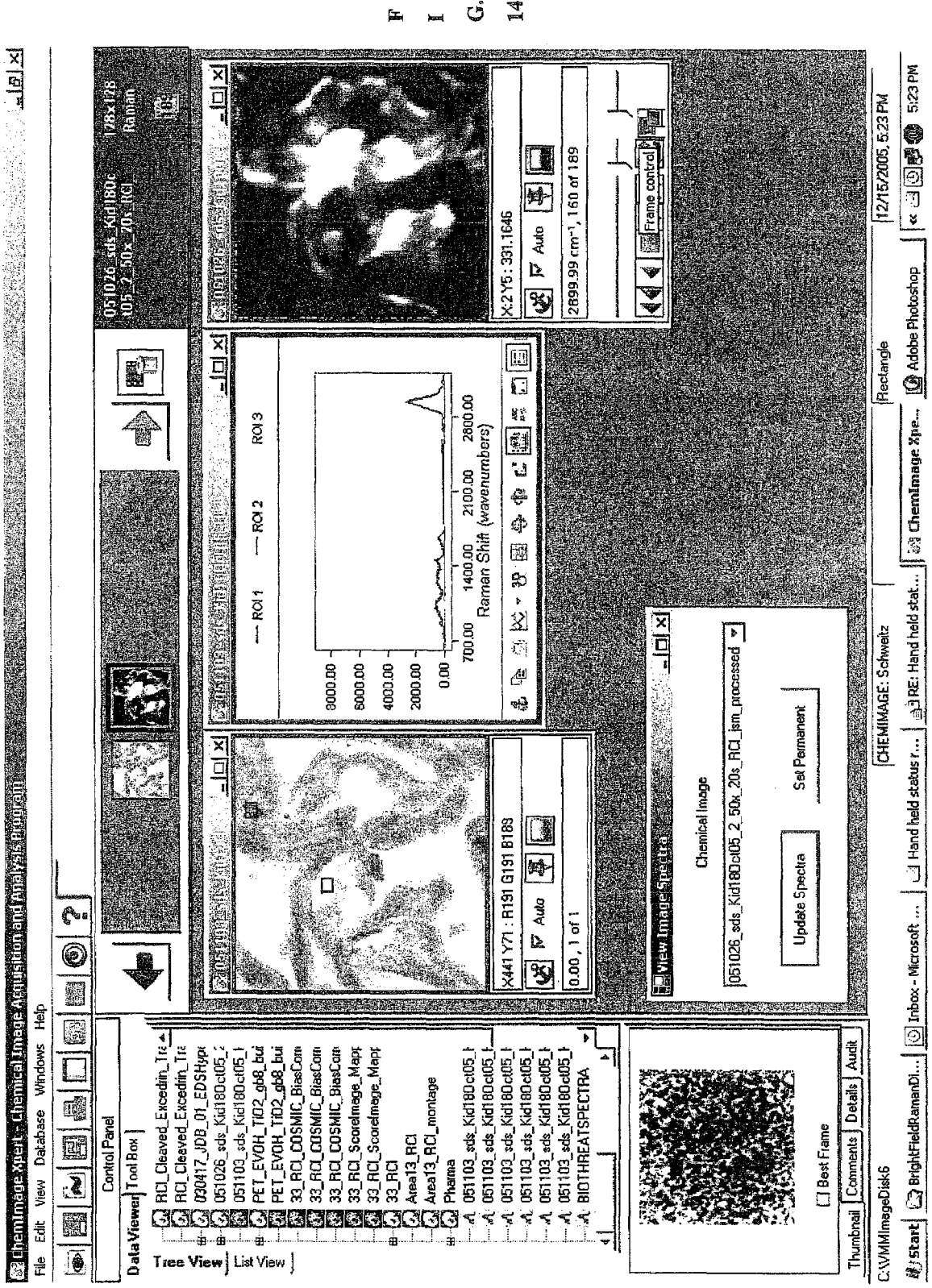
FIG. 14 shows an implementation of the disclosure for simultaneous display of regions-specific data on one frame.

FIG. 14 illustrates an exemplary display of such windows. Although the chemical image frame window (the far right window in FIG. 14) shows only the $160^{th}$ image frame out of the total of 189 image frames, the display functionality may be used in any manner to show either the combination of the brightfield image and ROI-specific spectra only or a chemical image frame along with the separate windows for brightfield image and region-specific spectra.

Furthermore, as shown above the brightfield images in FIGS. 11-14, a pair of thumbnail images showing the brightfield image and a frame of its corresponding (user-selected) Raman chemical image may also be displayed in a window pane to guide the user to the current image pair selection. The user may go forward/backward to view other non-current (prior) selections using the arrow buttons. It can be seen that the chemical image frame shown as a thumbnail may or may not be identical to the chemical image frame shown below the thumbnail view in a separate window along with the brightfield image window. In one embodiment, the larger view of the chemical image frame may be linked in software to the thumbnail view, allowing the user to update the thumbnail view by clicking on the larger view below.

FIG. 14 shows that three or more region-specific spectra that can be displayed in a single window for spectra of user-selected ROIs on a brightfield image. An additional window showing a frame of the Raman image (160th frame out of the total of 189 frames) corresponding to the selected brightfield image is also shown in FIG. 14 as mentioned before. The desired frame selection may be effected using a sliding pointer mechanism (identified by the "Frame control" text box overlayed adjacent to the slider mechanism) provided at the bottom of the frame window as illustrated in FIGS. 11-14.

As shown at FIGS. 11, 12 and 14, various image editing functionalities (e.g., image rotation, image zooming, text overlaying, etc.) may also be provided to allow the user to edit the image containing region-specific spectra. Additional or different processing features, as desired, may be provided in the software as may be evident to one skilled in the art. For example, trash can icon may be used to allow a user to discard/delete an image, such as an image shown as a thumbnail in the window pane above the brightfield image. The trash feature is illustrated on the right-hand side of the thumbnail-displaying window pane as can be seen from the screenshots in FIGS. 11-14.

In another embodiment, the software can be configured to automatically provide an indication whether the user-selected ROI is a biologically "good" (e.g., a healthy, non-cancerous region) or "bad" (e.g., a potentially cancerous region) area in the tissue sample. According to this embodiment, after the user selects an ROI, the software may be configured to carry out background calculations using selected ROI's associated spectrum (e.g., comparing the ROI-specific spectrum with a "standard" spectrum of a similar cell/tissue or of a similar location in a similar, but non-cancerous cell/tissue) to decide whether the ROI is "good" or "bad." The software can then automatically display its result in a pop-up window to alert the user to a potentially troublesome cell region. Such a feature may greatly assist a user (e.g., a doctor) in identifying potential regions of interest quickly and efficiently before spending time for further in-depth analysis or laboratory testing.

In a different embodiment, the window showing the brightfield image and the window showing the ROI-specific spectra may be displayed through different screen displays (not shown) instead of in a single screen display as is the case in the embodiments of FIGS. 11, 12 and 14. In that embodiment, the user may toggle between the two screens. In another embodiment, the ROI-specific spectrum may be displayed in an overlayed window (similar in nature to the overlayed text box marked "Frame control" in the Raman frame image window in FIG. 14) that is displayed on the computer screen when the user points a cursor at the selected region on the brightfield image. This overlayed window may disappear when the user removes the cursor away from a region selected on the brightfield image. When there are two or more selected regions, the overlayed window may display all ROI-specific spectra (similar, for example, to the three spectra displayed in a single window in FIG. 14) when a pointer is placed at any of the selected ROI. Other display methodologies may be devised, as desired, for displaying ROI-specific spectral information.

In one embodiment, the user may select an ROI in the brightfield image, copy the selected ROI using a "copy" function (not shown in the FIGS. 11-14), and then "paste" the selected ROI into the corresponding Raman or other chemical image frame being displayed along with the brightfield image. This action may instruct the software to scale the selected ROI onto the appropriate portion of the Raman image and display the corresponding ROI-specific spectral information. This approach illustrates a more manual approach than that explained with reference to embodiments discussed above.

The features shown in FIGS. 11-14 can be implemented using a software or a processor programmed with appropriate instructions. The implementation can also take place in a firmware. Further, the software or the processor can be configured as part of a system comprising an illumination source, detection optics and imaging devices.

EXAMPLES

Figure 4:
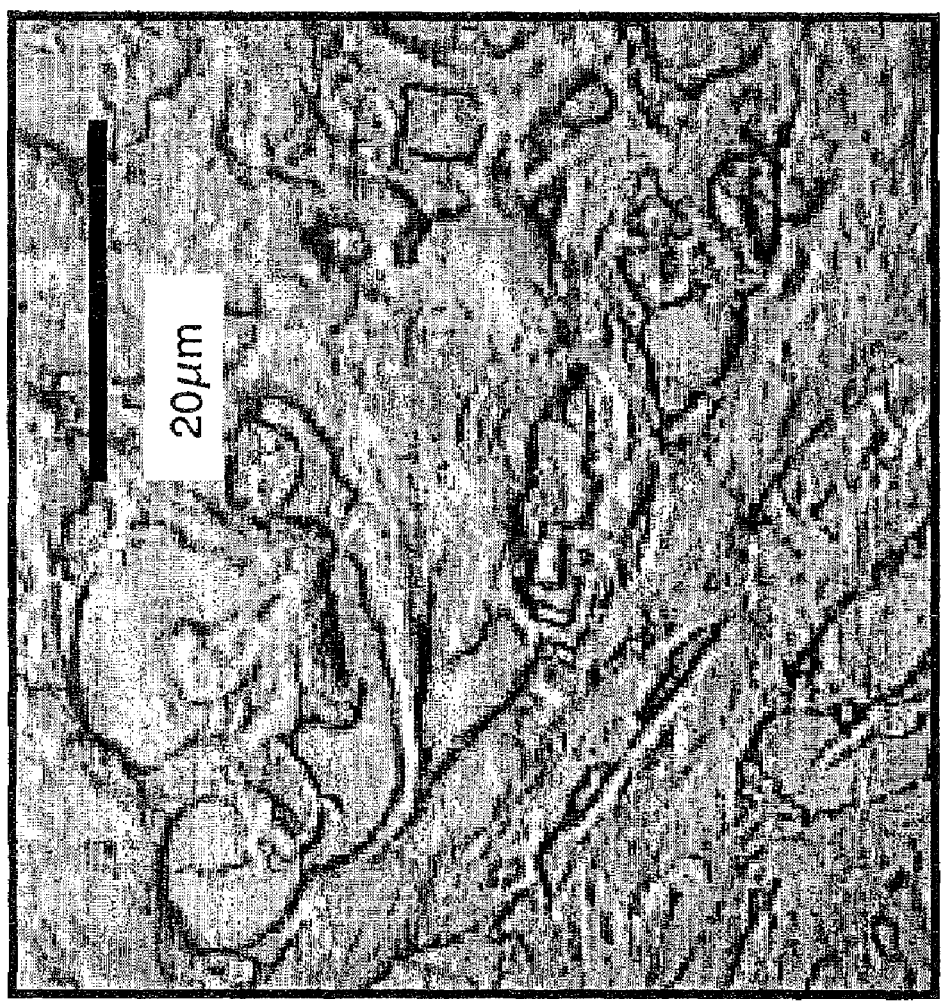
FIG. 4 shows a digital image of kidney tissue before treatment with a contrast enhancing agent obtained by an embodiment of the present disclosure.
Figure 7:
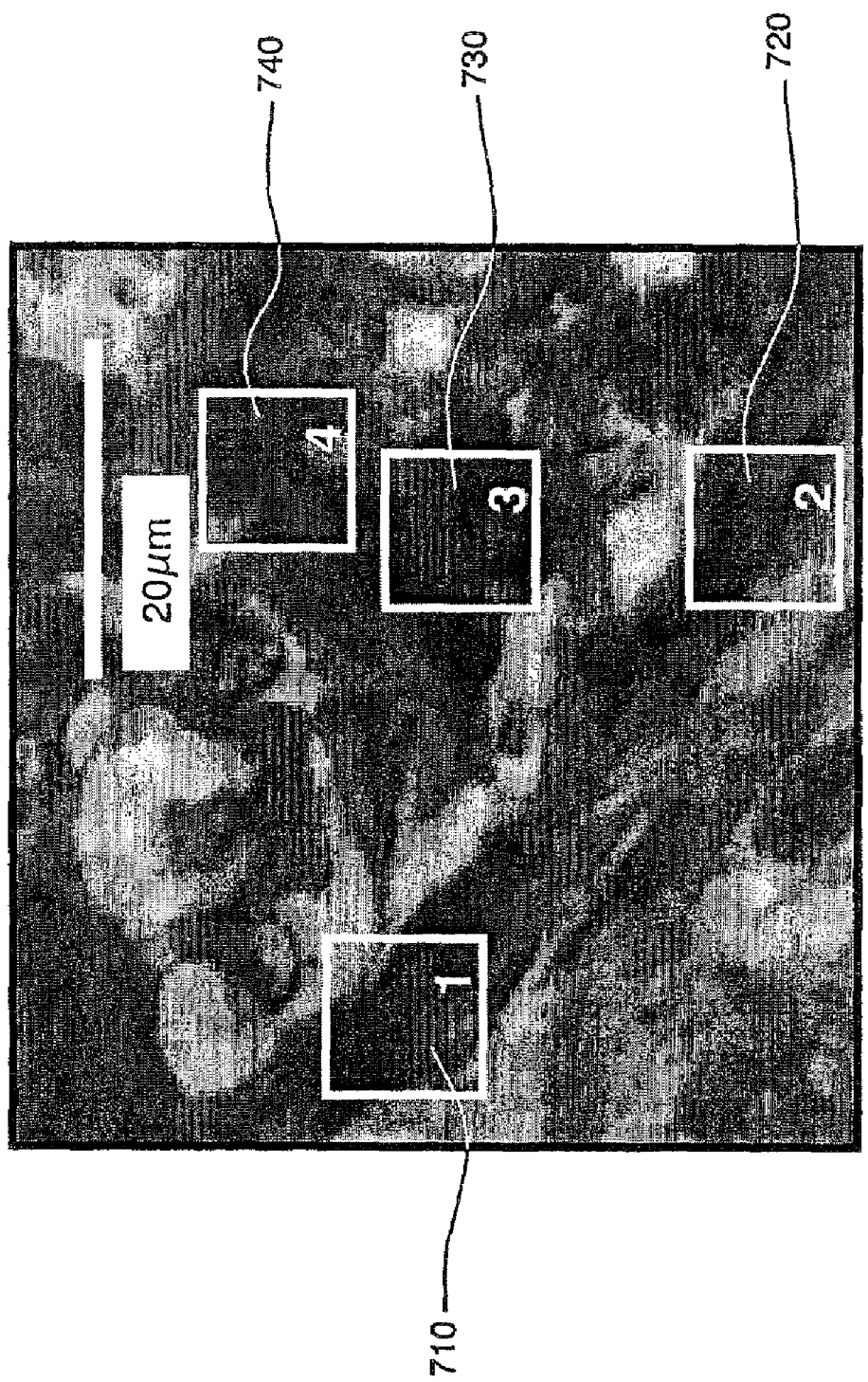
FIG. 7 shows a digital image of kidney tissue after treatment with a contrast enhancing agent.
Figure 8:
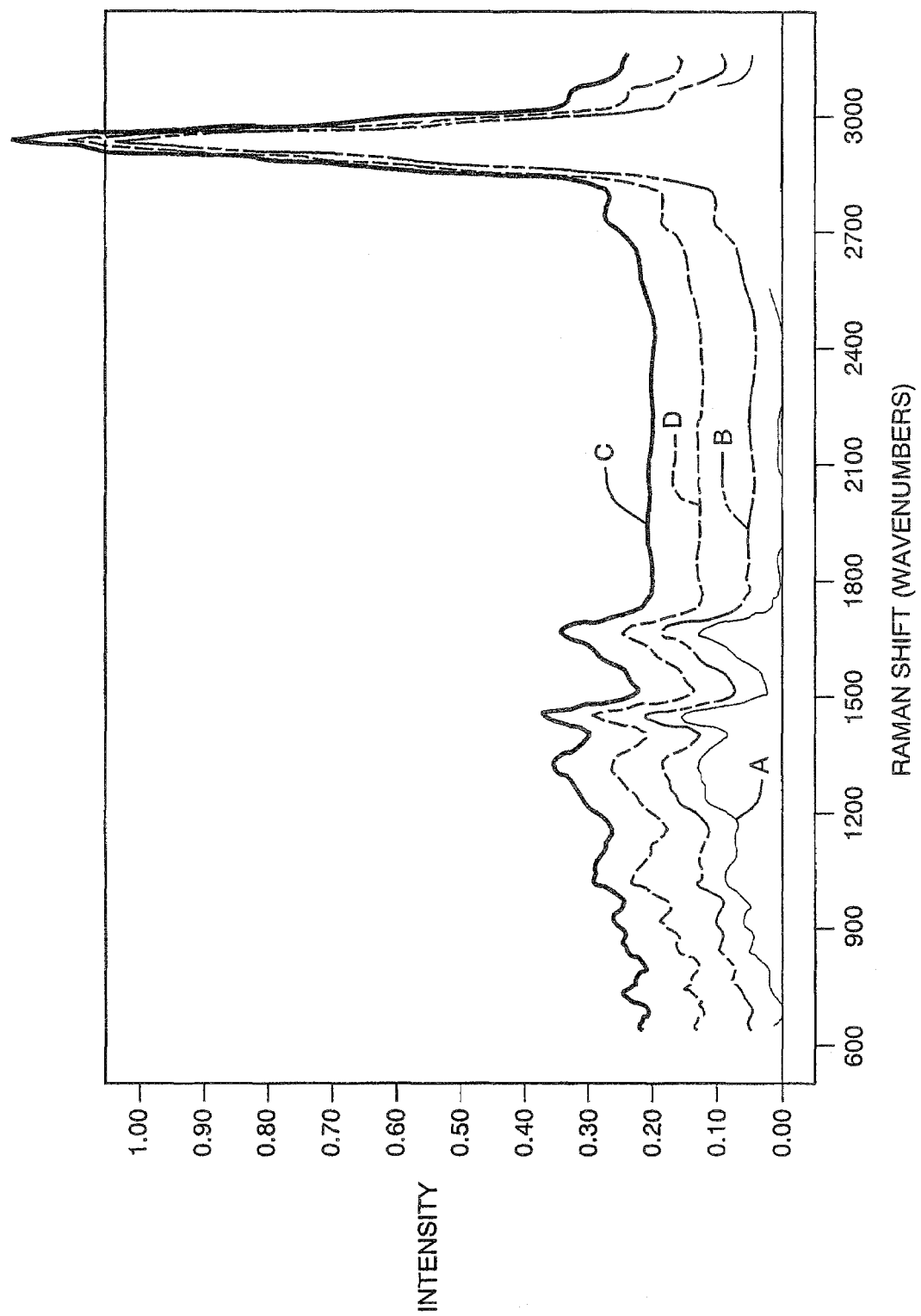
FIG. 8 shows Raman spectra for the corresponding regions of interest illustrated in FIG. 7.
Figure 9:
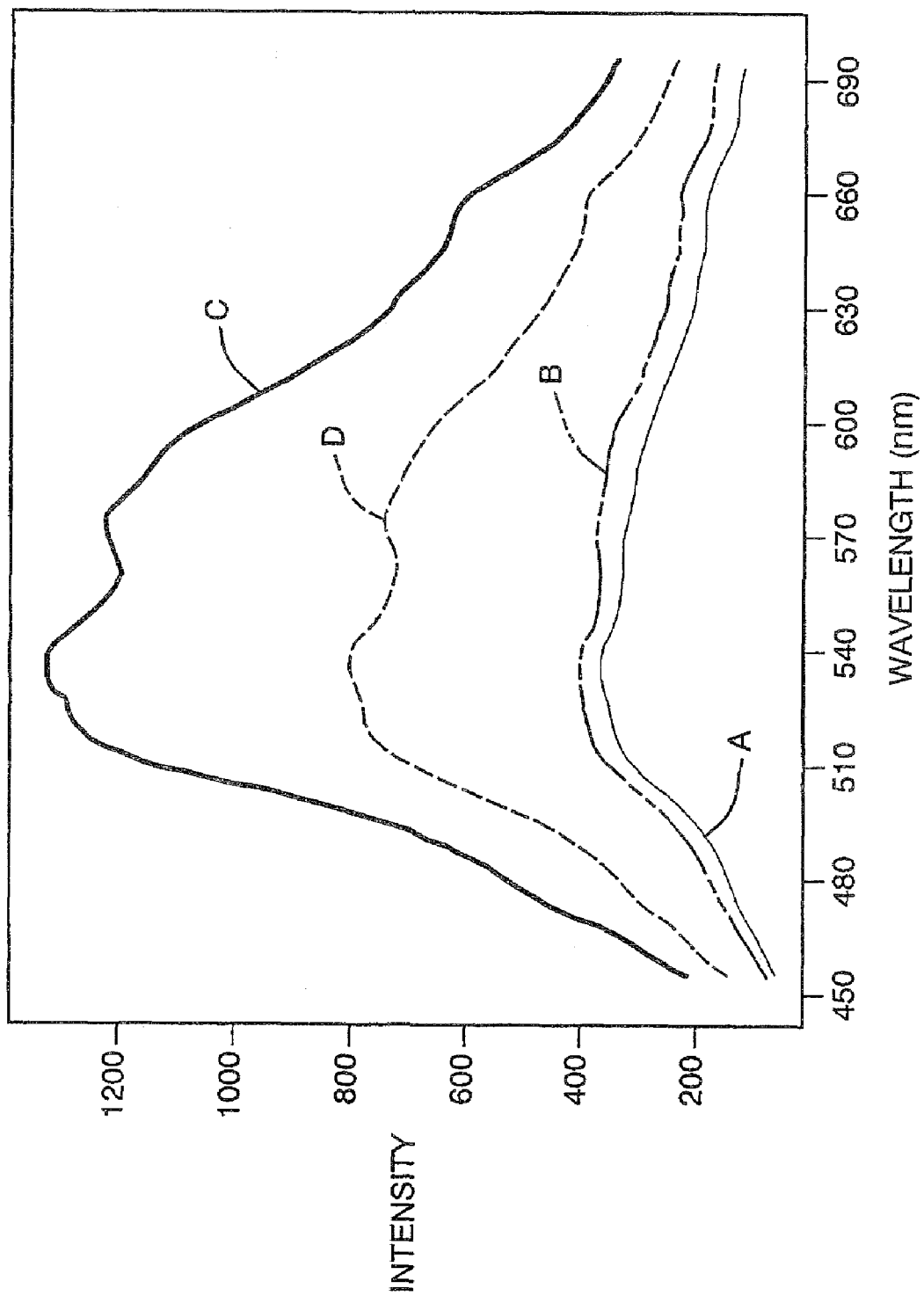
FIG. 9 shows fluorescence spectra for the corresponding regions of interest illustrated in FIG. 7.

Example 1 illustrates a set of image and spectroscopic data for a thin section of kidney tissue mounted on an aluminum coated slide. FIG. 4 shows a digital image for kidney tissue which has not been treated with a contrast enhancing agent. FIGS. 5A-5C show a series of Raman images of the kidney tissue of FIG. 4. FIG. 5A shows a spatially accurate Raman image at 1450 cm$^{-1}$. FIG. 5B shows a spatially accurate Raman image at 1650 cm$^{-1}$. FIG. 5C shows a spatially accurate Raman image at 2930 cm$^{-1}$. FIGS. 6A-B show a series of fluorescence images of the kidney tissue of FIG. 4. FIG. 6A shows a spatially accurate fluorescence image at 515 nm. FIG. 6B shows a spatially accurate fluorescence image at 570 rm. FIG. 7 shows a digital image of the kidney tissue after the tissue was stained with hematoxalin and eosin following standard staining procedures. FIG. 7 shows regions of interest 710, 720, 730 and 740 that are used to extract Raman and fluorescence data sets for searching. FIG. 8 illustrates a subset of Raman spectra for the regions of interest in FIG. 7 where the spectra were extracted from the corresponding regions of interest in the spectroscopic data set: Raman spectrum A corresponds to region of interest 710; Raman spectrum B corresponds to region of interest 720; Raman spectrum C corresponds to region of interest 730; and Raman spectrum D corresponds to region of interest 740. FIG. 9 illustrates fluorescence spectra for the regions of interest in FIG. 7 where the spectra were extracted from the corresponding regions of interest in the spectroscopic data set: fluorescence spectrum A corresponds to region of interest 710; fluorescence spectrum B corresponds to region of interest 720; fluorescence spectrum C corresponds to region of interest 730; and fluorescence spectrum D corresponds to region of interest 740.

Figure 10:
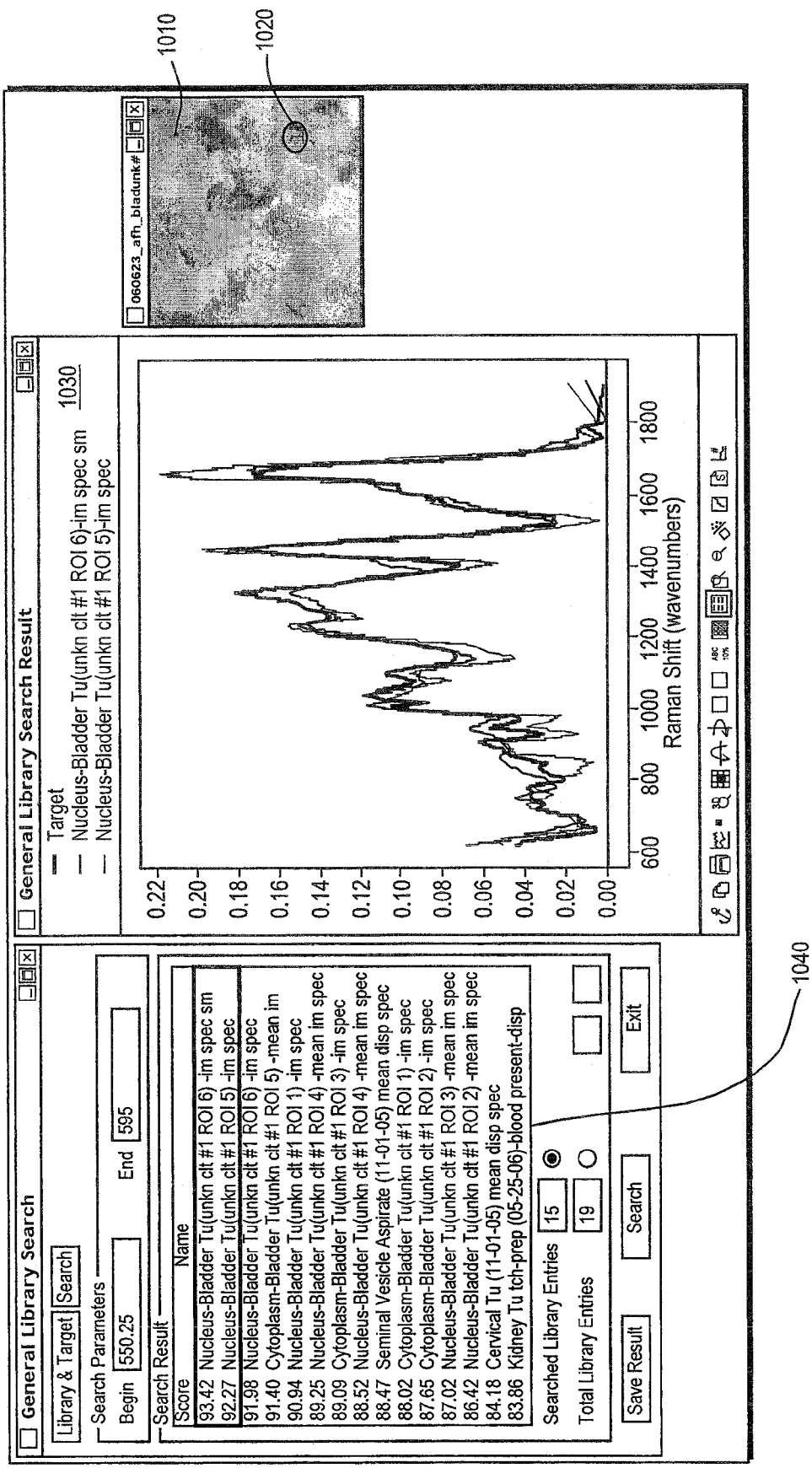
FIG. 10 shows an exemplary graphical user interface used to perform the method of the present disclosure.

FIG. 10 shows a graphical user interface for an embodiment of a system used in performance of a method of the present disclosure. A digital image 1010 is shown for a piece of bladder tissue stained with Hematoxalin and Eosin following standard staining procedures This digital image 1010 is linked to its Raman spectral dataset. The region of interest 1020 highlighted in the digital image is used to select a subset of the spectral data set for searching. The spectra data set is indicated in the spectral portion 1030 of FIG. 10. A subset of the spectral image dataset, in the form of a spectral trace, was searched against a database using Euclidian distance as a metric. The results of the search are evident in the left frame 1040. The correct classification of the region of interest is a nucleus from a bladder tumor. The disease classification of the samples in the database was obtained by pathological characterization. The spectra data search results, in the left frame 1040, identified nucleus from a bladder tumor as the top two ranked results.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed:

1. A method comprising:
    obtaining a digital image of a sample having a first plurality of pixels;
    obtaining a first spectroscopic data set of the sample, the spectroscopic data set corresponding to a second plurality of pixels;
    mapping the first plurality of pixels to the second plurality of pixels to associate the digital image of the sample with the first spectroscopic data set;
    selecting a first region of interest from the digital image of the sample, the first region of interest defined by a subset of the first plurality of pixels; and
    obtaining a second spectroscopic data set for the first region of interest by identifying a subset of the second plurality of pixels corresponding to the subset of the first plurality of pixels.

2. The method of claim 1, wherein the step of mapping the first plurality of pixels to the second plurality of pixels further comprises determining a spatial relationship between the first plurality of pixels and the second plurality of pixels.

3. The method of claim 1, wherein the step of mapping the first plurality of pixels to the second plurality of pixels further comprises mapping each of the first plurality of pixels to a corresponding pixel from the second plurality of pixels.

4. The method of claim 1, wherein the step of mapping the first plurality of pixels to the second plurality of pixels further comprises scaling the first plurality of pixels to spatially correspond to the second plurality of pixels.

5. A system comprising:
an optical device for obtaining a digital image of a sample and a first spectroscopic data set for the sample, the digital image defined by a first plurality of pixels and the first spectroscopic data set defined by a second plurality of pixels; and a processor programmed with instructions to:
map the first plurality of pixels to the second plurality of pixels to associate the digital image with the first spectroscopic data set;
identify a first region of interest from the digital image of the sample, the first region of interest defined by a subset of the first plurality of pixels; and
obtain a second spectroscopic data set for the first region of interest by identifying a subset of the second plurality of pixels corresponding to the subset of the first plurality of pixels.

6. The system of claim 5, further comprising a display for displaying one or more of the following: the digital image, the first spectroscopic data set, and the second spectroscopic data set.

7. The system of claim 5, wherein the optical device comprises a spectrometer.

8. The system of claim 5, wherein the optical device comprises means for obtaining a spatially accurate wavelength resolved image of the sample.

9. The system of claim 5, wherein the processor is further programmed with instructions to determine a spatial relationship between the first plurality of pixels and the second plurality of pixels.

10. The system of claim 5, wherein the processor is further programmed with instructions to map each of the first plurality of pixels to a corresponding pixel from the second plurality of pixels.

11. The system of claim 5, wherein the processor is further programmed with instructions to scale the first plurality of pixels to spatially correspond to the second plurality of pixels.

* * * * *